United States Patent
Olive et al.

[11] Patent Number: 5,709,662
[45] Date of Patent: Jan. 20, 1998

[54] CARTRIDGE FOR AN INJECTION DEVICE

[75] Inventors: Eric Olive, Lyons, France; Bernard Sams, London, United Kingdom

[73] Assignee: Becton Dickinson France, S.A., Claix, France

[21] Appl. No.: 701,963

[22] Filed: Aug. 23, 1996

[51] Int. Cl.$^6$ .................................................. A61M 5/20
[52] U.S. Cl. .................... 604/135; 604/110; 604/130; 604/157; 604/192; 604/198; 604/187
[58] Field of Search ................................. 604/130, 131, 604/132, 133, 134, 135, 136, 137, 138, 192, 198, 263, 110, 156, 157

[56] References Cited

U.S. PATENT DOCUMENTS

| | | | |
|---|---|---|---|
| 2,752,918 | 7/1956 | Uytenbogaart | 128/218 |
| 3,797,489 | 3/1974 | Sarnoff | 128/218 |
| 4,484,910 | 11/1984 | Sarnoff et al. | 604/136 |
| 4,565,543 | 1/1986 | Bekkering et al. | 604/135 |
| 4,822,340 | 4/1989 | Kamstra | 604/135 |
| 4,902,279 | 2/1990 | Schmidtz et al. | 604/136 |
| 5,085,642 | 2/1992 | Sarnoff et al. | 604/135 X |
| 5,092,842 | 3/1992 | Bechtold et al. | 604/135 |
| 5,102,393 | 4/1992 | Sarnoff et al. | 604/135 X |
| 5,104,384 | 4/1992 | Parry | 604/198 X |
| 5,114,404 | 5/1992 | Paxton et al. | 604/110 |
| 5,137,516 | 8/1992 | Rand et al. | 604/136 |
| 5,176,643 | 1/1993 | Kramer et al. | 604/135 |
| 5,273,544 | 12/1993 | Van Der Wal | 604/135 X |
| 5,320,609 | 6/1994 | Haber et al. | 604/135 |
| 5,334,144 | 8/1994 | Alchas et al. | 604/135 X |
| 5,358,489 | 10/1994 | Wyrick | 604/135 X |
| 5,391,151 | 2/1995 | Wilmot | 604/135 X |
| 5,425,715 | 6/1995 | Dalling et al. | 604/135 X |
| 5,472,430 | 12/1995 | Vaillancourt et al. | 604/198 |
| 5,478,316 | 12/1995 | Bitdinger et al. | 604/135 |
| 5,514,097 | 5/1996 | Knauer | 604/198 X |
| 5,540,664 | 7/1996 | Wyrick | 604/135 X |
| 5,567,160 | 10/1996 | Massion | 604/135 X |
| 5,569,192 | 10/1996 | Van Der Wal | 604/135 X |

*Primary Examiner*—Sam Rimell
*Assistant Examiner*—Robert V. Racunas
*Attorney, Agent, or Firm*—V. A. Castiglione

[57] ABSTRACT

An assembly for automatically injecting a fluid into the body is provided. The assembly includes a drive assembly, which can be reused many times, and a disposable assembly including a sleeve which contains a syringe. The drive assembly includes a housing having an open end to which a collar is mounted. The collar includes a radially inwardly extending pawl. The sleeve includes a generally cylindrical body having a radially outwardly extending rib. The rib defines a notch which is engageable with the pawl when the disposable assembly is inserted within the drive assembly housing. Engagement of the pawl within the notch prevents the disposable assembly from being ejected from the drive assembly housing should the actuating button of the drive assembly be pushed prematurely. Ejection of the disposable assembly requires its rotation with respect to the drive assembly housing to first disengage the pawl from the notch.

15 Claims, 14 Drawing Sheets

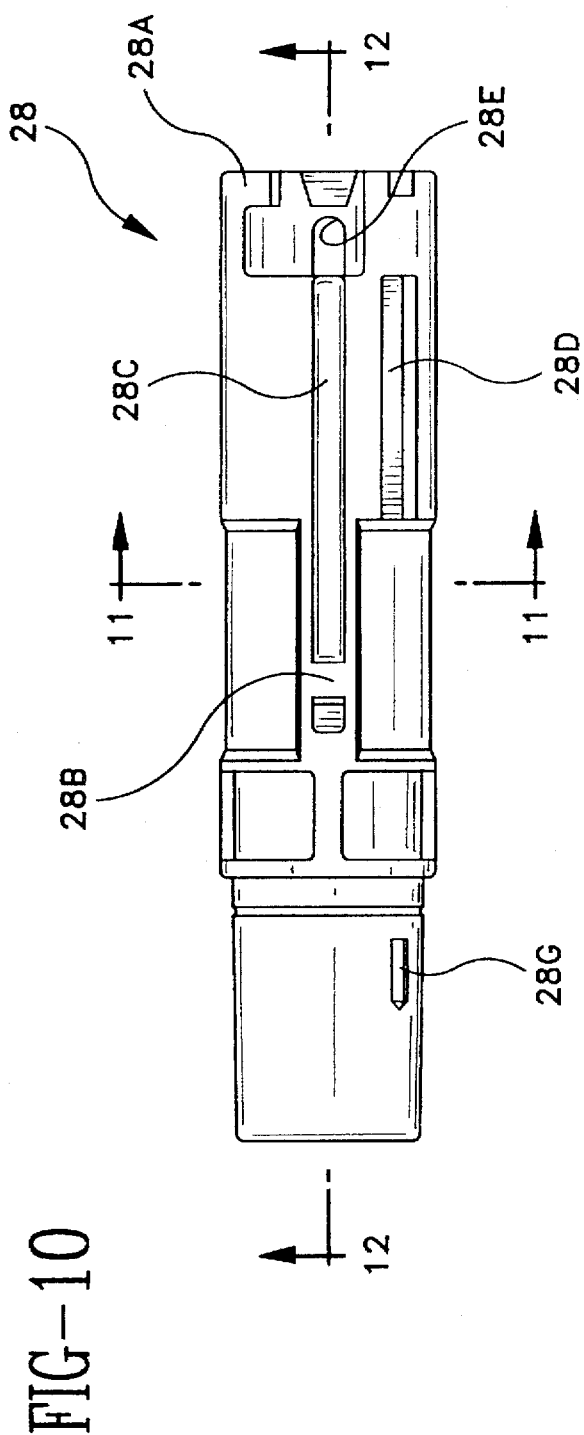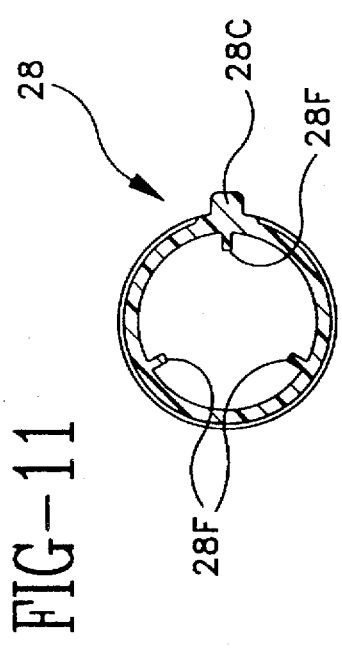
FIG-10
FIG-11

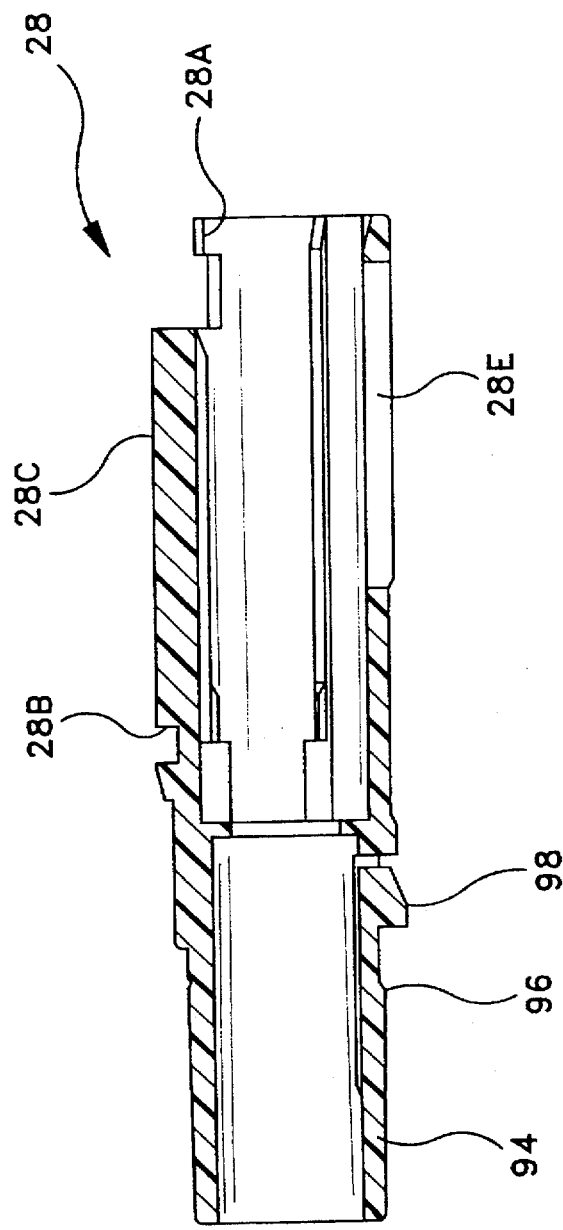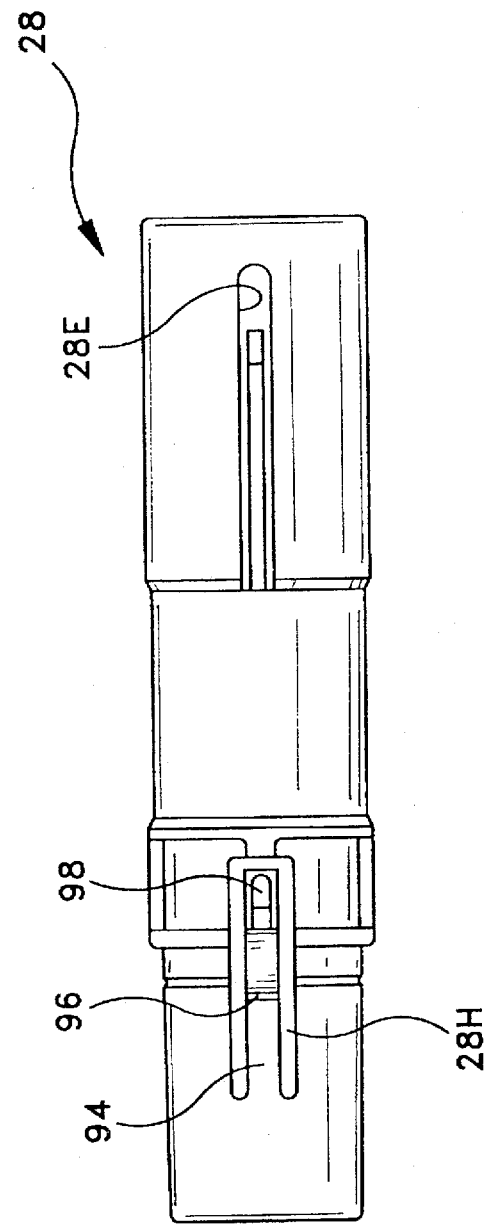

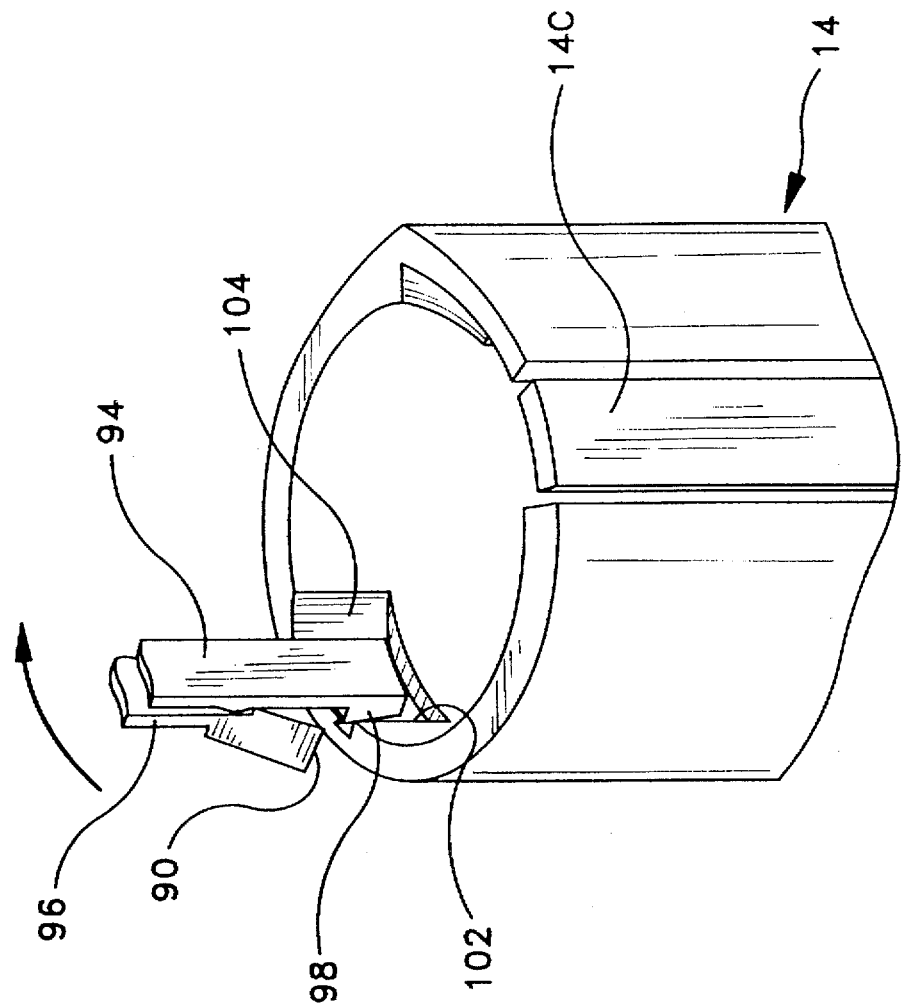

CARTRIDGE FOR AN INJECTION DEVICE

BACKGROUND OF THE INVENTION

1. Field of the Invention

The field of the invention relates to injection devices for automatically dispensing premeasured quantities of material, and disposable assemblies therefor.

2. Brief Description of the Prior Art

Injection devices such as syringes are widely used in the medical and veterinary fields. They are ordinarily employed by trained personnel who are capable of selecting the appropriate medication and administering the required dosage.

Specialized injection devices have been designed for situations where trained personnel are not available to administer medication. Such devices are usable by persons such as diabetics who self-inject insulin, allergy sufferers who may require an emergency injection of anti-histamines or other medication, and other patients where self-injection is either more convenient or necessary.

U.S. Pat. No. 2,752,918 discloses one type of automatically operated injection device. Upon firing an actuating mechanism of this device, a needle is caused to penetrate the skin, medicament is injected through the bore of the needle, and the needle is retracted. The device includes a first coil spring for causing the needle to be projected beyond a nose piece and a second coil spring which is compressed during this procedure. The second spring, upon release of a clutch mechanism, then automatically urges an arepule and stem rearwardly, causing retraction of the needle.

U.S. Pat. No. 5,137,516 discloses another type of automatically operated injection device. The user first presses the device against the skin in order to move an internal shaft and sleeve assembly. An actuating button is then depressed, causing a button arm to spread the arms of a retention clip. The separation of these arms releases the head of the pusher rod, which is then moved forwardly under the force of a main coil spring. The pusher rod first moves the entire syringe against the force of a syringe spring. Once the needle has penetrated the skin, the syringe plunger is depressed by the pusher rod, causing the syringe to empty. The main spring of the patented device may be recocked upon reloading of a new syringe assembly. Such reloading is accomplished by a force applied by the syringe piston directly upon the pusher rod of the device.

U.S. Pat. No. 5,478,316 discloses a device including a drive assembly and a disposable syringe assembly coupled thereto. The drive assembly includes a constant force spring which urges the syringe assembly in such a manner that the syringe needle is first caused to enter a patient's skin. This step is followed by the injection of fluid through the needle into the patient.

The syringe assembly of the patented device includes, inter alia, a sleeve and a cap. The cap is mounted to one end of the sleeve, and protects the needle prior to use of the device. As the cap does not rotate with respect to the sleeve, it may be grasped by the user during the process of coupling the syringe assembly to the drive assembly.

The drive assembly of the patented device includes a housing which is coupled to a collar. The collar includes a slot which, during installation of the syringe assembly, is aligned with a longitudinal rib extending radially outwardly from the sleeve. This sleeve can be pushed into the housing of the drive assembly when so aligned, thereby loading the spring. The syringe assembly is then rotated, causing engagement of the push button of the drive assembly with a projection at one end of the sleeve.

A number of other approaches have been taken for providing automatic injection of various materials. U.S. Pat. Nos. 3,797,489, 4,484,910, 4,902,279, 5,114,404 and 5,425,715 provide further examples of this type of device.

SUMMARY OF THE INVENTION

An autoinjector is provided which includes a drive assembly and a disposable assembly including a sleeve and a syringe. The disposable assembly is removably securable to the drive assembly, as the drive assembly is intended to be reused.

The drive assembly and disposable assembly are constructed such that the disposable assembly cannot be ejected by the drive assembly until it is moved to the firing position. In other words, the loading of the disposable assembly to the drive assembly must be completed, and the drive assembly fired, before the disposable assembly can be uncoupled from the drive assembly.

An assembly according to the invention includes a drive assembly including a housing and a drive rod. A spring is provided for resiliently urging the drive rod. The disposable portion of the assembly includes a sleeve and a syringe assembly slidably mounted within the sleeve. The syringe assembly includes a cartridge and a piston slidably mounted within the cartridge. The drive rod is operatively associated with the syringe assembly when the sleeve is mounted within the drive assembly housing, and causes fluid to be expelled from the cartridge when actuated by the user.

The sleeve is slidably positioned within the housing when an injection is to be made. In order to prevent the sleeve and its contents from being prematurely expelled, one of the sleeve and drive assembly housing is provided with a stop member, while the other is provided with an engagement member. In accordance with a preferred embodiment of the invention, the sleeve includes an elongate rib including a notch which defines a stop member, while the housing includes a radially inwardly extending pawl which defines the engagement member. The engagement member is positioned to engage the stop member as the sleeve is positioned within the housing, thereby preventing its removal. Removal may be accomplished only after the sleeve has been moved to the firing position, which is preferably accomplished by rotation of the sleeve about its longitudinal axis. Such rotation causes displacement of the engagement member with respect to the stop member.

BRIEF DESCRIPTION OF THE DRAWINGS

FIG. 10 is a bottom plan view of the sleeve of the injection device;

FIG. 11 is a sectional view thereof taken along line 11—11 of FIG. 10;

FIG. 12 is a sectional view thereof taken along line 12—12 of FIG. 10;

FIG. 13 is a top plan view of the sleeve;

FIG. 14 is a cutaway perspective view showing the insertion of the sleeve into the collar of the drive assembly;

DETAILED DESCRIPTION OF THE INVENTION

An injection device 10 is provided which is particularly adapted for the self-administration of medicines and other materials. The device is similar in structure and operation to that described in U.S. Pat. No. 5,478,316, which is incorporated by reference herein.

Figure 1:
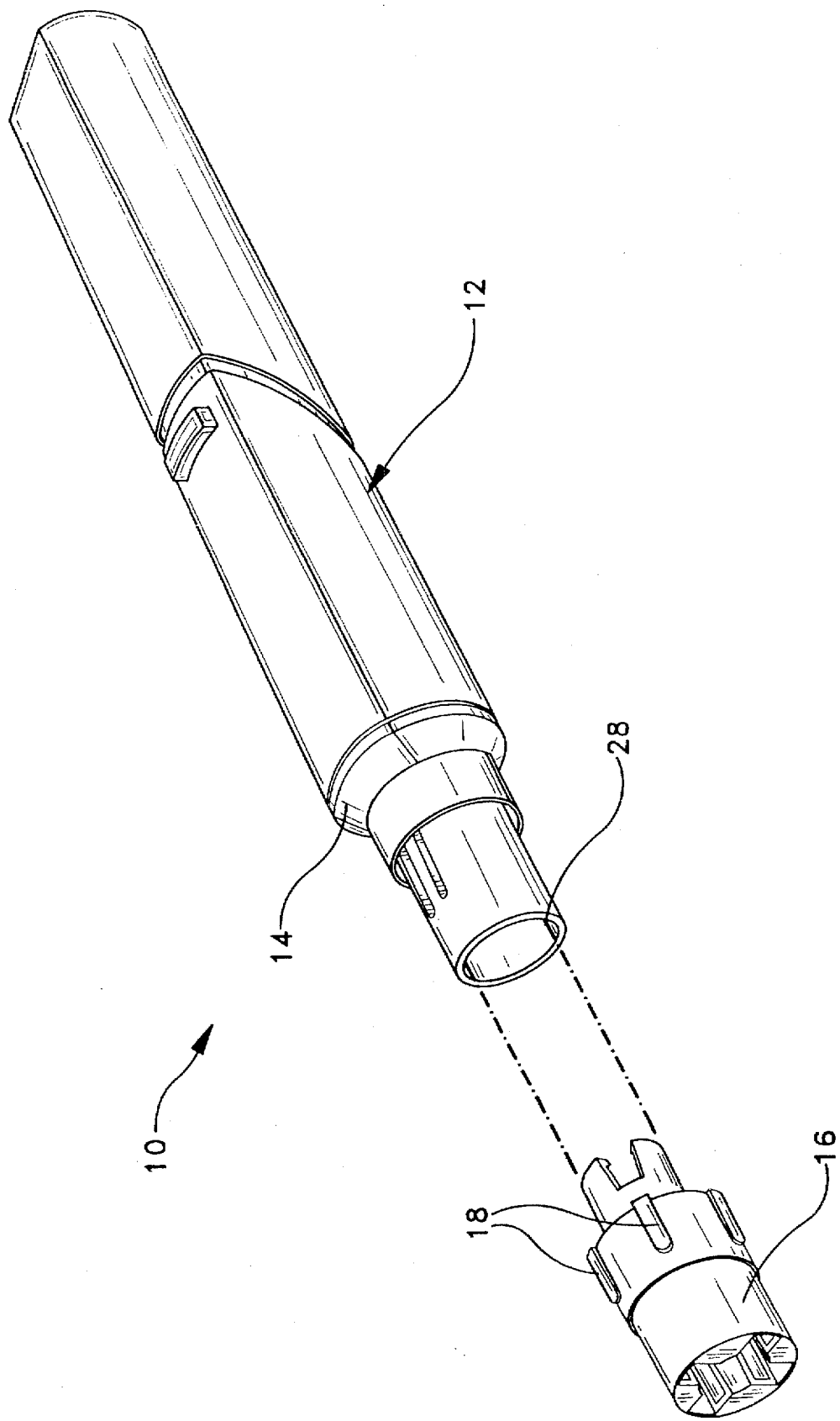
FIG. 1 is a partially exploded, top perspective view of an injection device according to the invention.
Figure 2:
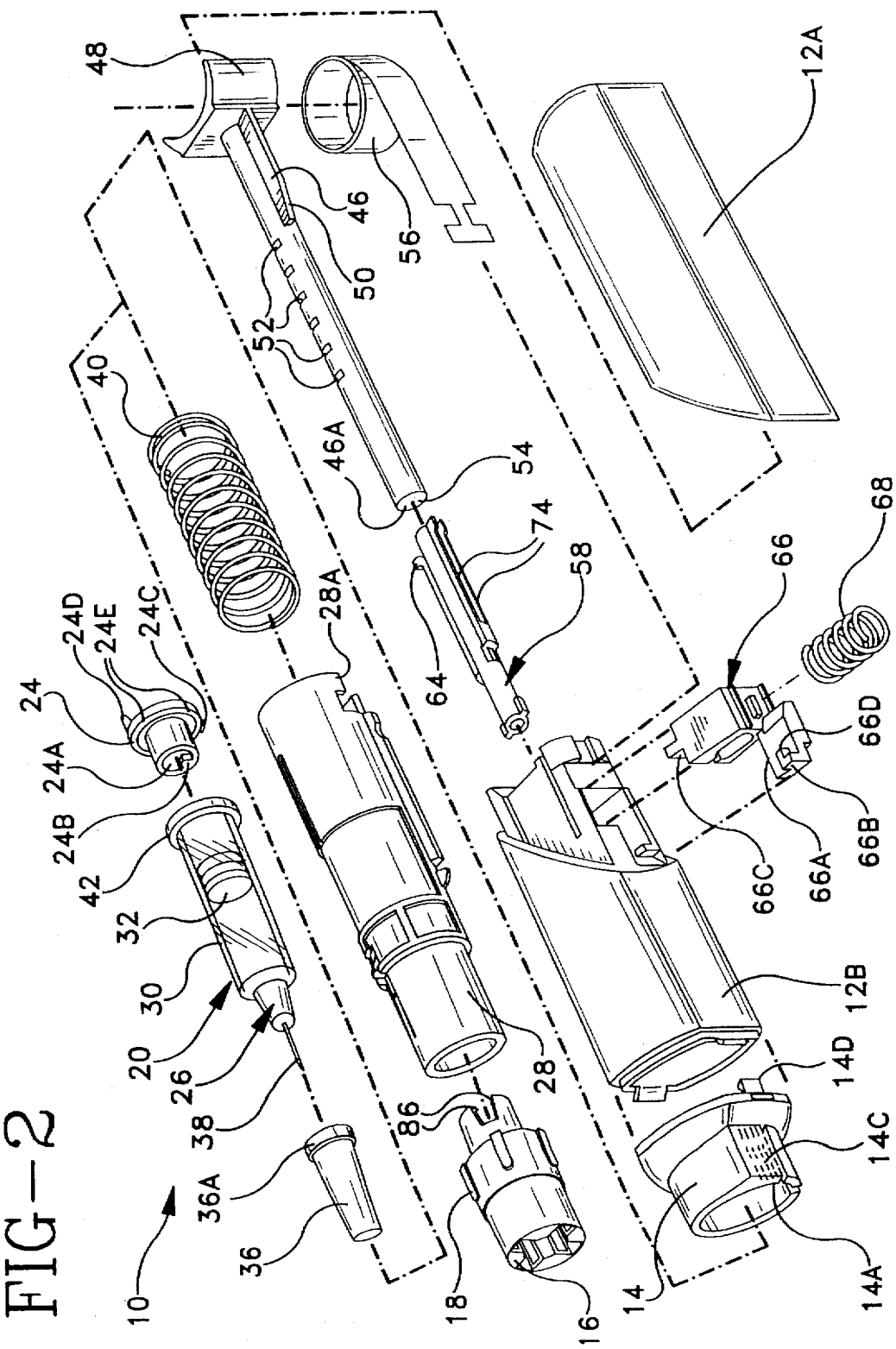
FIG. 2 is an exploded, perspective view of the device.

Referring to FIGS. 1 and 2, the device includes a drive assembly including an elongate housing 12 which may be easily handled by a user. One end of the housing is closed, while the opposite end is mounted to a collar 14. The collar is permanently mounted to the housing 12, and may be considered a part of the housing. A cap 16 is mounted to one end of a sleeve 28 in adjoining relation to the collar. The cap is not rotatable upon the sleeve, and is employed in conjunction with the collar for mounting a syringe assembly to the drive assembly. A plurality of elongate ribs 18 on the exterior surface of the cap are used during the mounting procedure, which is described in detail below.

Figure 3:
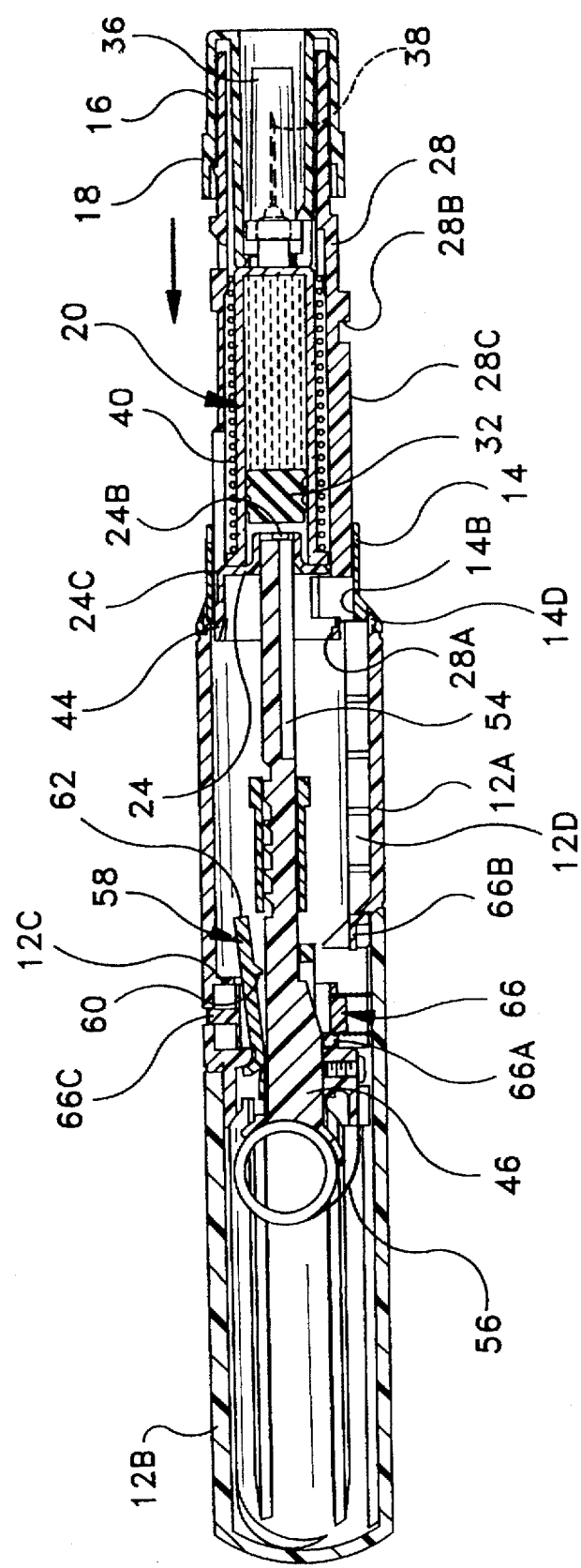
FIG. 3 is a sectional view showing the initial step in mounting a new syringe assembly to the drive assembly.
Figure 4:
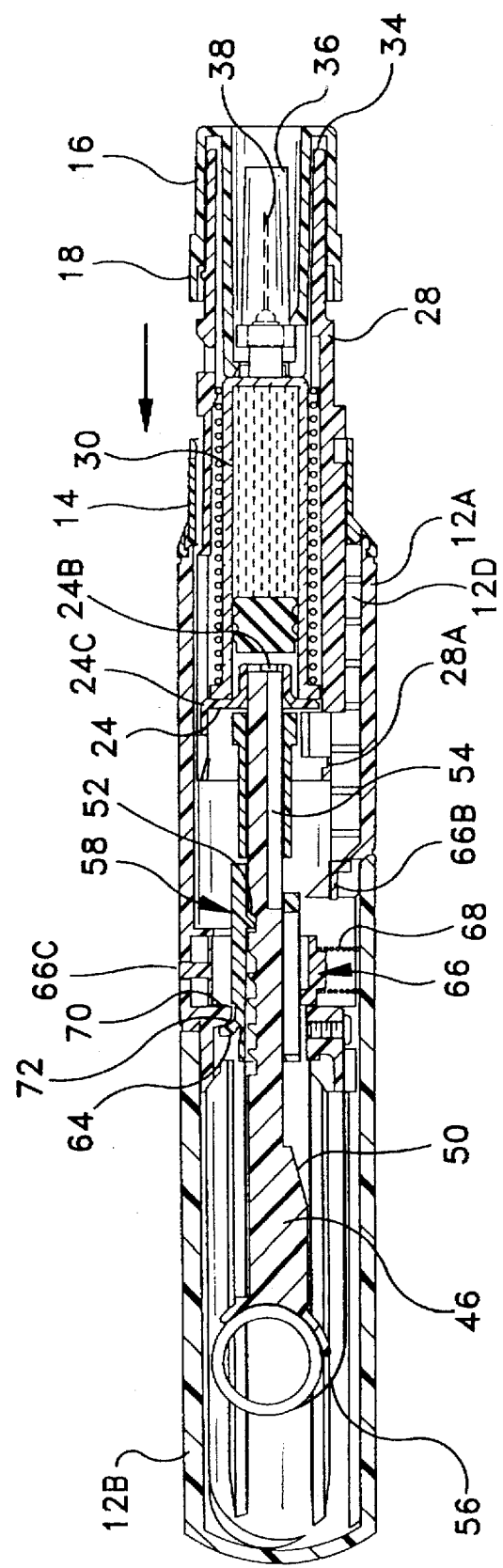
FIG. 4 is a similar view showing the new syringe assembly partially within the housing of the drive assembly.

Referring to FIGS. 2–4, a syringe assembly 20 is provided in accordance with the preferred embodiment of the invention. A plug 24 is mounted to one end of the syringe assembly, and a needle assembly 26 is mounted to the opposite end thereof. The sleeve 28 encloses the syringe assembly. The syringe assembly includes a cartridge 30 or barrel and a piston 32 slidably positioned within the cartridge. The cap 16 is removably mounted to one end of the sleeve. An annular slot 34 is defined by a pair of concentric walls of the cap. The end portion of the sleeve 28 is positioned within the annular slot.

A rubber shield 36 is positioned within the cap, and protects the needle 38 of the syringe assembly. The shield is frictionally retained by the cap, and is removable with the cap when the device is to be employed. Rotation of the cap causes rotation of the syringe assembly 20 and sleeve 28 with respect to the drive assembly when a new syringe and sleeve assembly is secured thereto.

A coil spring 40 is provided for resiliently urging the sleeve 28 with respect to the cartridge 30. The cartridge includes a flange 42 which abuts against one end of the spring. The other end of the spring engages a radially inwardly extending wall of the sleeve. A portion 44 of the sleeve extends behind the plug 24, thereby preventing the sleeve and plug from being disconnected from the syringe assembly. The spring 40 causes the sleeve to extend over the needle in its rest position, as shown in FIG. 3.

The drive assembly of the device is designed for repeated use. The drive assembly housing 12 is comprised of two sections 12A, 12B secured to each other by ultra-sonic welding or other suitable procedure. An elongate drive rod 46 is positioned within the housing. Guide rails 47 integral with the housing 12 maintain the orientation of the rod. The rod 46 includes an integral saddle 48 at one end thereof. The opposite end of the rod is smaller in dimension such that it fits within the plug 24 and cartridge 30. A ramp 50 is defined on one side of the rod near the saddle end thereof. The opposite side of the rod includes a plurality of notches 52. An elongate groove 54 extends from the end of the rod within the cartridge for a distance corresponding to at least the maximum length of travel of the piston 32 within the cartridge 30.

A constant force spring 56 is provided for urging the rod 46 in the direction of the piston 32. The wound end of the spring 56 is cradled within the saddle 48. The other end of the spring is secured to the housing 12. While a coil spring could be used to propel the rod, such a spring does not exert a substantially constant force upon the rod as it moves axially through the housing. In order to insure that a coil spring exerts sufficient force at the end of the stroke of the rod, it must be compressed more than is actually required at the beginning of the stroke. This results in a relatively high impact upon the syringe assembly by the driving mechanism, and ultimately upon the epidermis of the patient. Such a driving mechanism is also more likely to be very audible to the user, which may tend to upset the user.

The force exerted by the constant force spring 56 is sufficient to overcome the friction between the piston 32 and the cartridge 30 and between the needle 38 and the user's skin. When the rod 46 is pushed back to the start position after firing, the user needs to exert only a constant force upon the rod. If a coil spring was employed in the drive assembly, a steadily increasing force would be required to reload the device.

A driver 58 is releasably coupled to the rod 46. The driver includes a generally cylindrical body through which the rod 46 extends. A radially inwardly extending pawl 60 is positionable within one of the notches 52 for connecting the driver to the rod. The pawl 60 extends from a deflectable spring arm 62 of the driver. One end of the arm includes a radially outwardly extending projection 64. One end of the driver abuts against the plug 24. Driver 58 also includes a pair of axially-aligned flats 74.

A push-button 66 is provided for engaging both the driver 58 and the sleeve 28. The push-button accordingly functions as retaining means for retaining the rod/driver assembly and the constant force spring in the storage position, as well as an actuating member for releasing the retaining means. Referring to FIG. 3, the push-button includes a first engagement member 66A which releasably engages the driver. (Alternatively, the rod could be releasably engaged). It further includes a second engagement member 66B which engages a projection 28A of the sleeve. The second engagement member prevents the sleeve from being removed from the drive assembly when the sleeve is rotated to the firing position, and also prevents the push-button from being inadvertently actuated.

Figure 5:
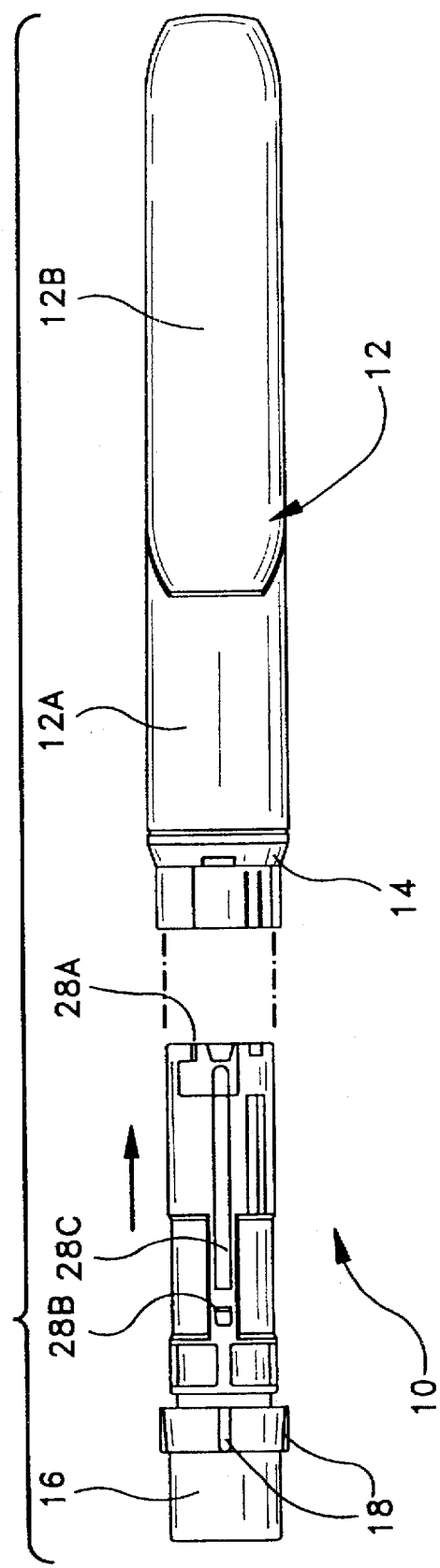
FIG. 5 is a side elevation view showing the coupling of a new sleeve and syringe assembly to the drive assembly.
Figure 6:
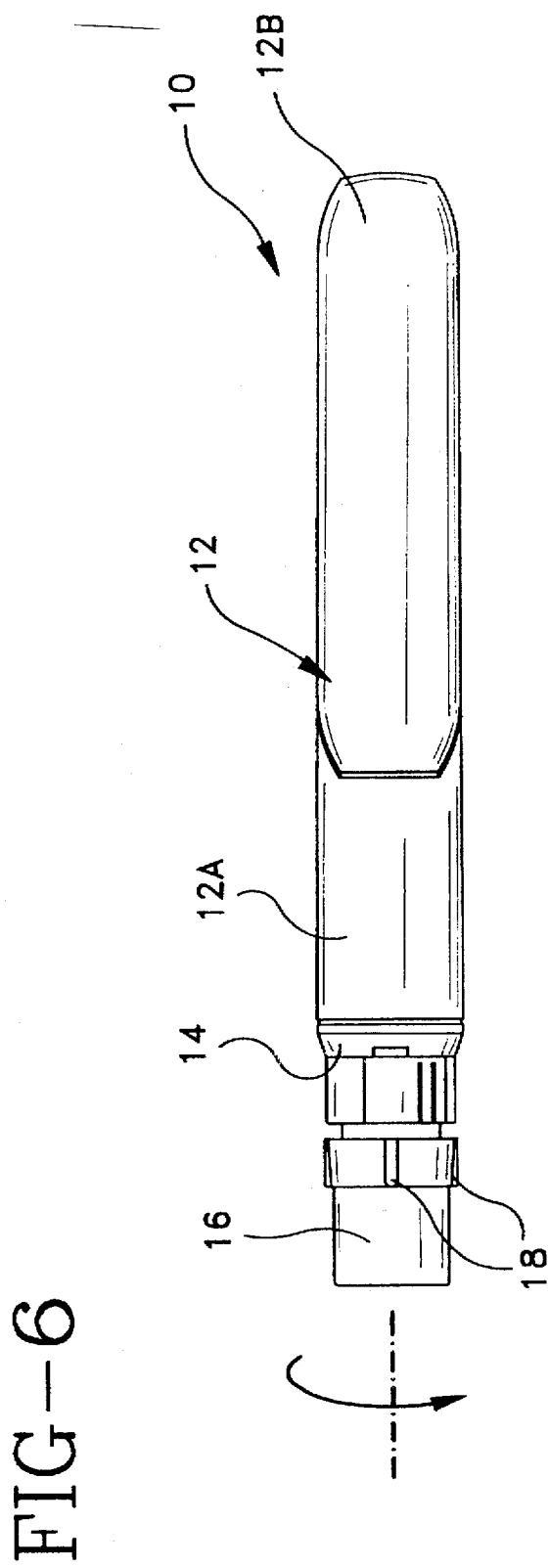
FIG. 6 is a side elevation view showing the final step in mounting a new sleeve and syringe assembly to the drive assembly.

The push-button further includes a projection 66C which is extendible through an opening in the housing 12. The push-button and projection are maintained in the position shown in FIG. 1 by a coil spring 68 as shown in FIG. 4 which urges the push-button towards the opening, as well as by the sleeve projection 28A. When the sleeve projection is displaced rearwardly, as shown in FIG. 5, the coil spring 68 alone maintains the position of the push-button.

The first engagement member 66A of the push-button may be moved out of engagement with the driver 58 upon manually urging the push-button against the force of the compression spring 68. Upon further travel of the driver/rod assembly, the ramp 50 defined on one side of the rod 46 engages the first engagement member 66A, thereby drawing the push-button further inside the housing 12. This movement causes the release of the sleeve 28, which is urged by the sleeve spring 40 into a position covering the tip of the needle 38.

As discussed above, the plug 24 is mounted to one end of the syringe assembly 20, and an end of the driver 58 engages the plug. The plug includes an opening 24A (FIG. 2) through which the rod 46 passes when an injection is made. The plug further includes an abutment in the form of a radially inwardly extending projection 24B, as shown in FIGS. 2–4. The syringe assembly is rotatable between a first position, where the projection 24B abuts an end surface 46A of the rod, and a second position where the projection 24B is opposite the groove 54 in the rod. The rod is accordingly able to pass through the plug when the syringe assembly is in the second rotational (i.e., firing) position. About forty degrees of rotation are required to move the syringe assembly between the first and second positions.

The plug 24 further includes a radially outwardly extending projection 24C which is located within a first axial slot 28D in the sleeve. An axial projection 24D extends from the plug, and may be used for alignment purposes when a new syringe assembly is loaded. The axial projection 24D is positioned within a second axial slot 28E formed in the sleeve. The engagement of these projections 24C, 24D with the rear walls of the respective slots 28D, 28E prevent the syringe assembly from being moved out of the sleeve under the force of the coil spring 40. Three equidistantly spaced notches 24E are formed in the outer surface of the plug. The sleeve includes three axially extending ribs 28F projecting from the inner surface thereof, as shown in FIG. 11. These ribs 28F extend within the notches 24E, thereby maintaining the desired orientation of the plug with respect to the sleeve.

The housing 12 includes means for engaging the projection 64 of the driver, thereby causing the arm 62 thereof to pivot about an integral hinge portion. This, in turn, causes the pawl 60 to be withdrawn from the notch 52. The engaging means include a radially inwardly extending projection 70 having an arcuate surface which engages a corresponding arcuate surface on the projection 64. Driver 58 further includes a squared surface 72 adjacent projection 64. Squared surface 72 engages a distally-facing portion of projection 70 to prevent inadvertent return of needle 38.

Figure 7:
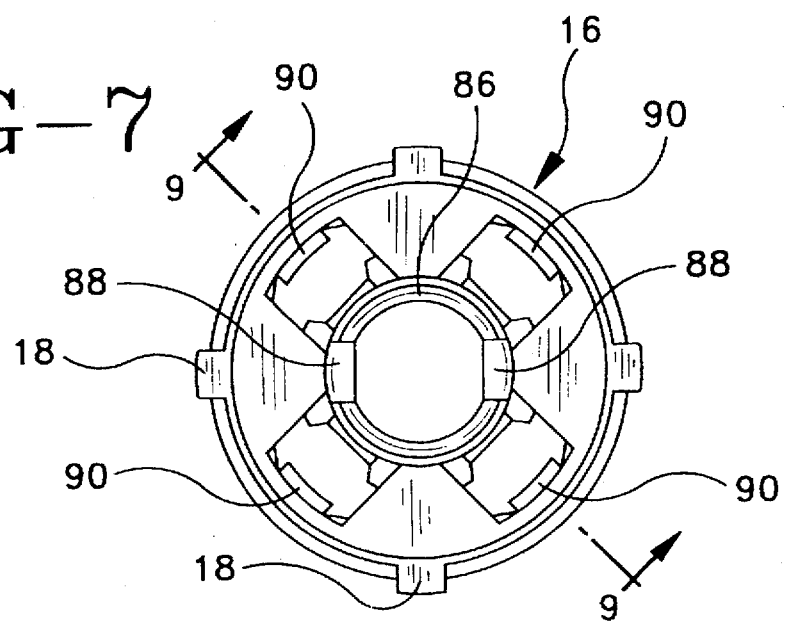
FIG. 7 is a top plan view of the injection device.
Figure 8:
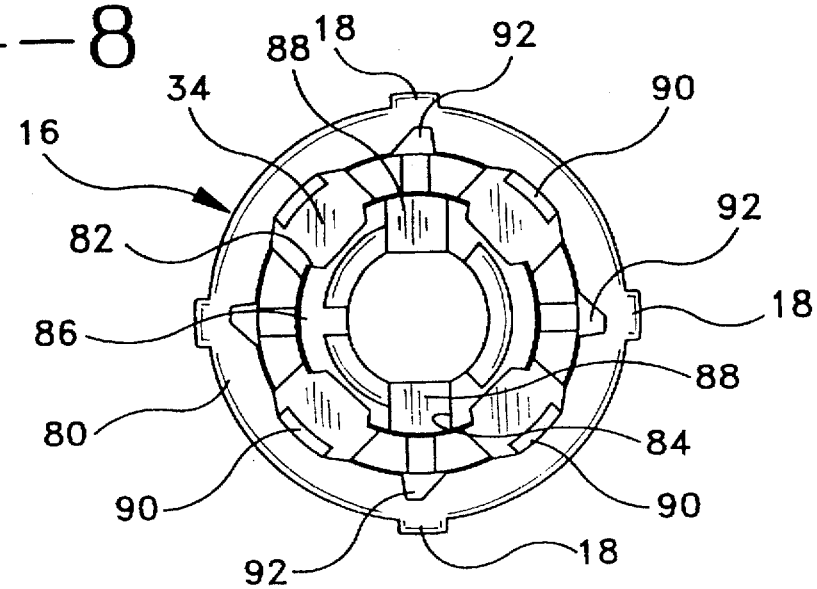
FIG. 8 is a bottom plan view thereof.
Figure 9:
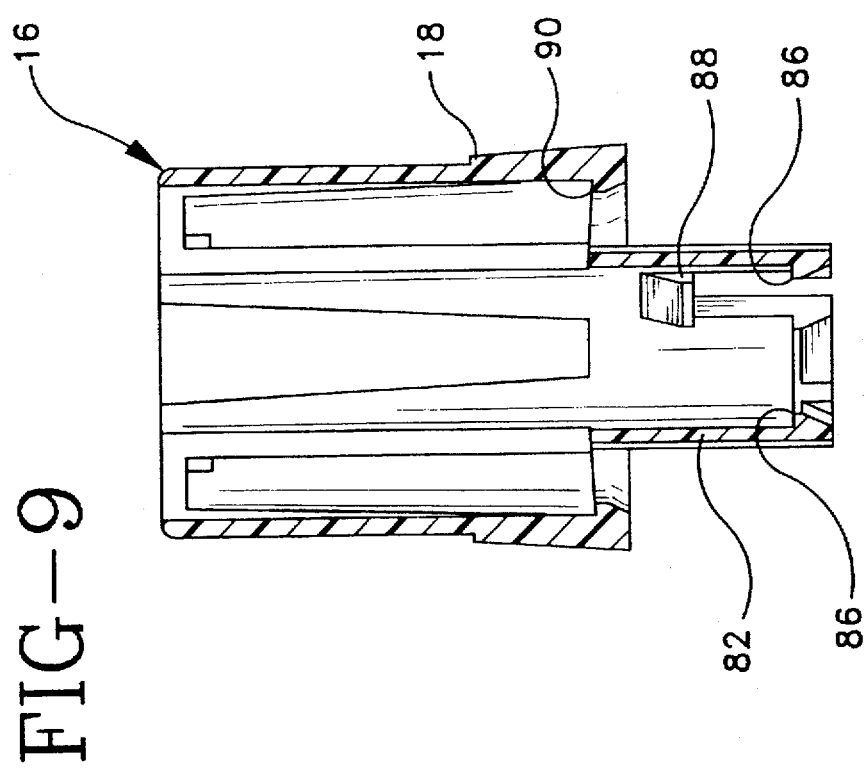
FIG. 9 is a sectional view taken along line 9—9 of FIG. 7.
Figure 16:
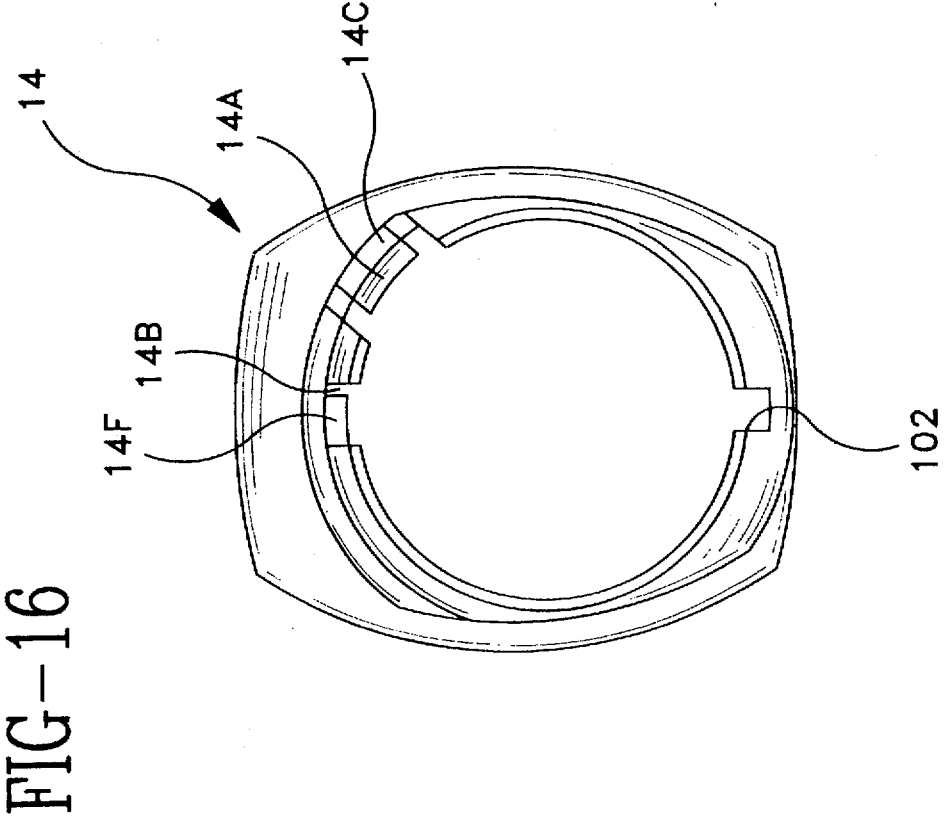
FIG. 16 is a top plan view of the collar.
Figure 15:
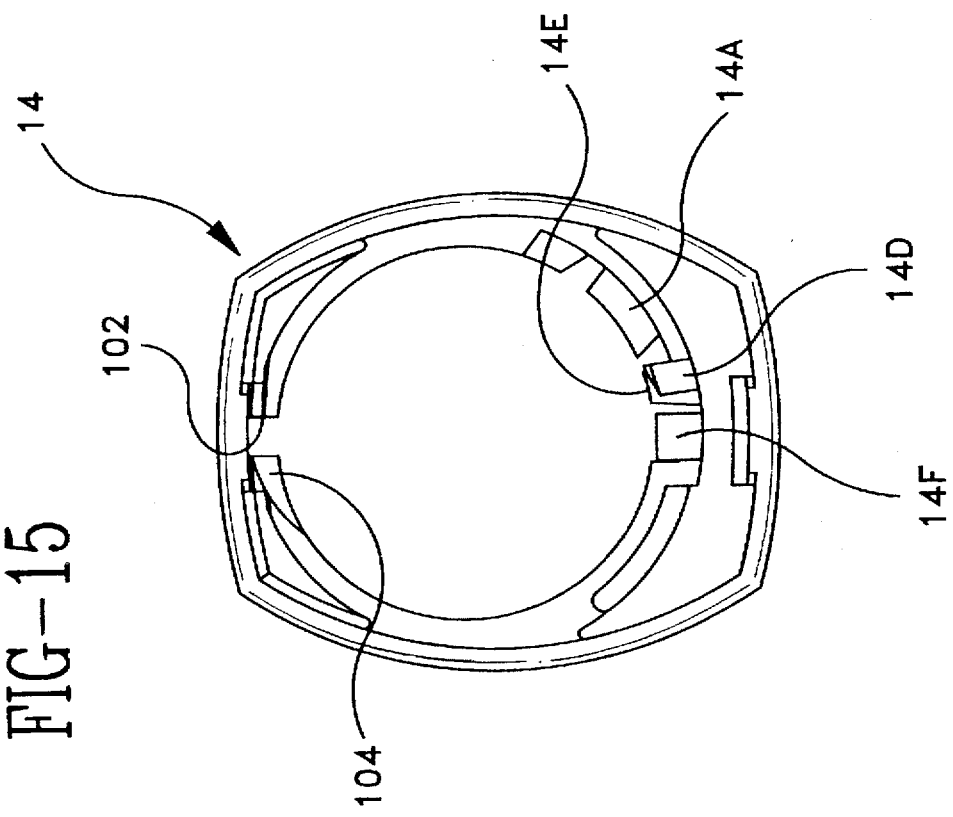
FIG. 15 is a bottom plan view of the collar.
Figure 18:
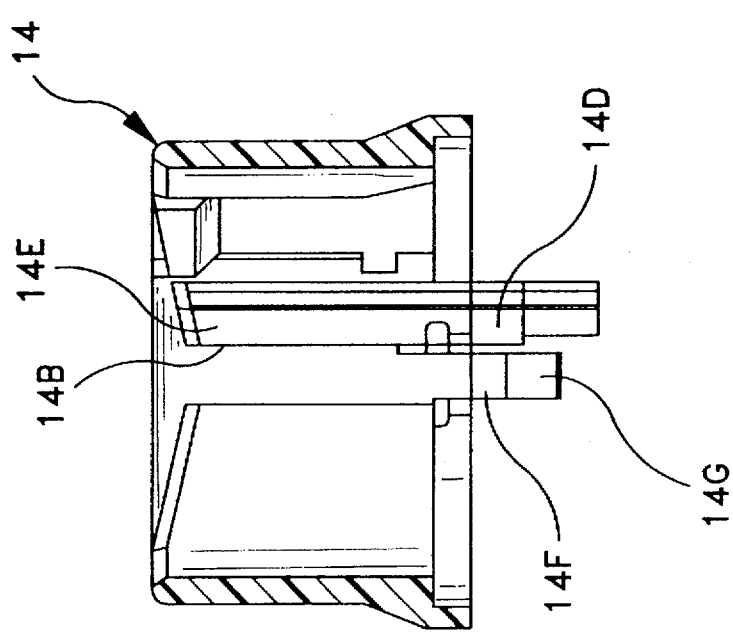
FIG. 18 is a sectional view taken along line 18—18 of FIG. 17.
Figure 17:
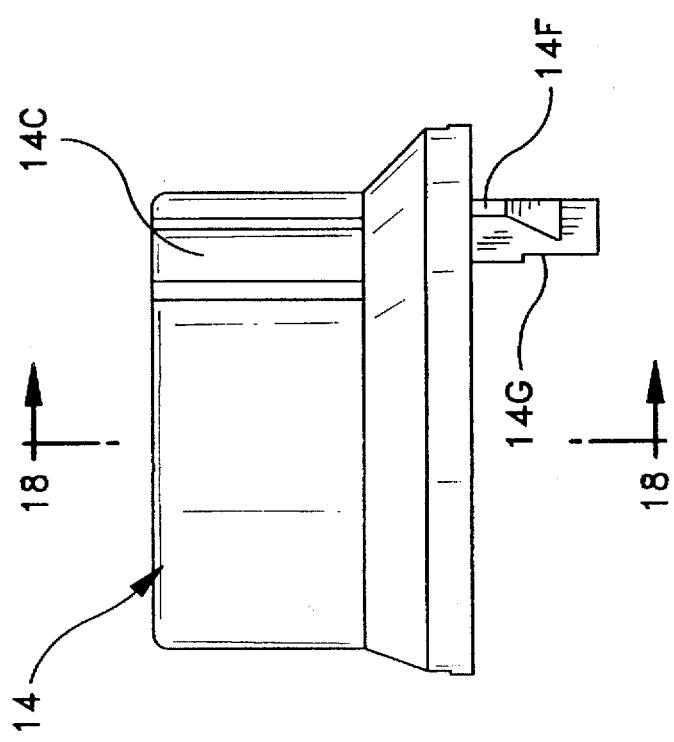
FIG. 17 is a side elevation view of the collar.

FIGS. 7–9 provided detailed views of the cap 16 which is mounted to the open end of the sleeve 28. The cap includes a generally cylindrical outer wall 80 having four radially projecting ribs 18. The cap further includes a generally cylindrical inner wall 82 which is coaxial with the outer wall 80. The inner wall 82 includes a pair of opposing slots 84 at the bottom end thereof. Each of the opposing wall portions adjoining the slots includes a radially inwardly extending rim 86. A radially inwardly extending projection 88 is formed at the top of each slot 84. The rubber shield 36 for the needle 38, shown in FIG. 2, includes a relatively thick wall 36A at its open end which is maintained between the rim 86 and projections 88.

Two pairs of opposing, radially inwardly extending projections 90 are integral with the lower end of the outer wall 80 of the cap. As discussed below, these projections function as locking members which are engageable with a locking member on the sleeve 28. Each projection 90 includes a beveled lower surface and a top surface which extends substantially perpendicularly with respect to the longitudinal axis. The beveled surface initially engages a locking member on the cap, allowing the locking member to snap behind the projection when axial force is exerted on the cap.

Two pairs of opposing grooves 92 are formed in the inner surface of the outer wall 80 of the cap. Each groove has a generally saw-toothed configuration in cross section. The grooves adjoin the end surface of the outer wall, as shown in FIG. 8, and are aligned with the respective ribs 18.

FIGS. 10–13 provide detailed views of the sleeve 28 of the injection device. The sleeve includes a generally cylindrical body having a longitudinal rib 28C extending from its lower surface. A notch 28B including a pair of vertical edges is defined near the from portion of the rib 28C. A relatively short rib 28G extends from the outer surface of the front portion of the sleeve, and is designed to fit within any of the grooves 92 in the inner surface of the cap 16.

The front portion of the sleeve further includes an elongate, deflectable finger 94, which is preferably integral with the sleeve body as shown. The finger includes a first, relatively small projection or rib 96 and a second, relatively large saw-toothed projection 98. The end of the finger near the front end of the sleeve is integral with the sleeve body. The opposite end is free. The finger is positioned within an elongate slot 28H, and is deflectable about its connection to the sleeve body into the slot. Other than the two projections 96, 98, the finger is generally flush with the outer surface of the front portion of the sleeve.

The first, relatively small projection 96 of the finger 94 functions as a locking member when engaged with one of the radially extending projections 90 within the cap 16. The short rib 28G and grooves 92 ensure that the locking members 96, 90 are aligned when the cap is mounted to the sleeve. Once the projection 96 has snapped behind one of the cap projections 90, the cap cannot be removed until the finger 94 is deflected well into the slot 28H. This can be accomplished manually by pushing the large projection 98 towards the slot 28H. It is preferably accomplished, however, by mounting the sleeve to the drive assembly and moving it into the firing position, as schematically shown in FIG. 14.

FIGS. 15–18 provide detailed views of the collar 14, which is designed for interacting with the sleeve in an advantageous manner. The collar includes a base which is snapped onto the drive assembly housing 12. A generally cylindrical portion is integral with the base.

A first finger 14C including a pawl extends from the collar base to the rim. An axial slot 14B is provided within the inner surface of the cylindrical portion of the collar. The slot 14B is located about forty degrees from the finger 14C. A projection 14D extends downwardly from the cylindrical portion, and is located between the slot 14B and finger 14C. When the collar is mounted to the housing 12, the projection 14D is positioned in opposing relation to an axial rib 12D extending from the inner surface thereof. A channel is defined between the projection 14D and rib 12D for receiving the longitudinal rib 28C of the sleeve 28. The channel is aligned with the slot 14B in the collar. The projection 14D includes an inclined surface 14E which allows a portion of the sleeve rib 28C to be rotated from the slot 14B into a second slot having a bottom wall defined by the finger 14C. Inclined surface 14E prevents sleeve 28 from deviating from its rotational position once it has been rotated in place by a user.

A second finger 14F including a second pawl 14G is positioned in alignment with the slot 14B. The second finger is deflectable about its connecting point to the cylindrical portion of the collar, and is substantially parallel to the first finger 14C. The second pawl 14G is oriented such that the second finger is deflected by the longitudinal rib 28C of the sleeve as the sleeve is mounted to the drive assembly. The second pawl enters the notch 28B within the rib when the sleeve has been fully inserted. The sleeve is accordingly prevented from being withdrawn from the drive assembly housing once the second pawl has entered the sleeve notch.

Figure 19:
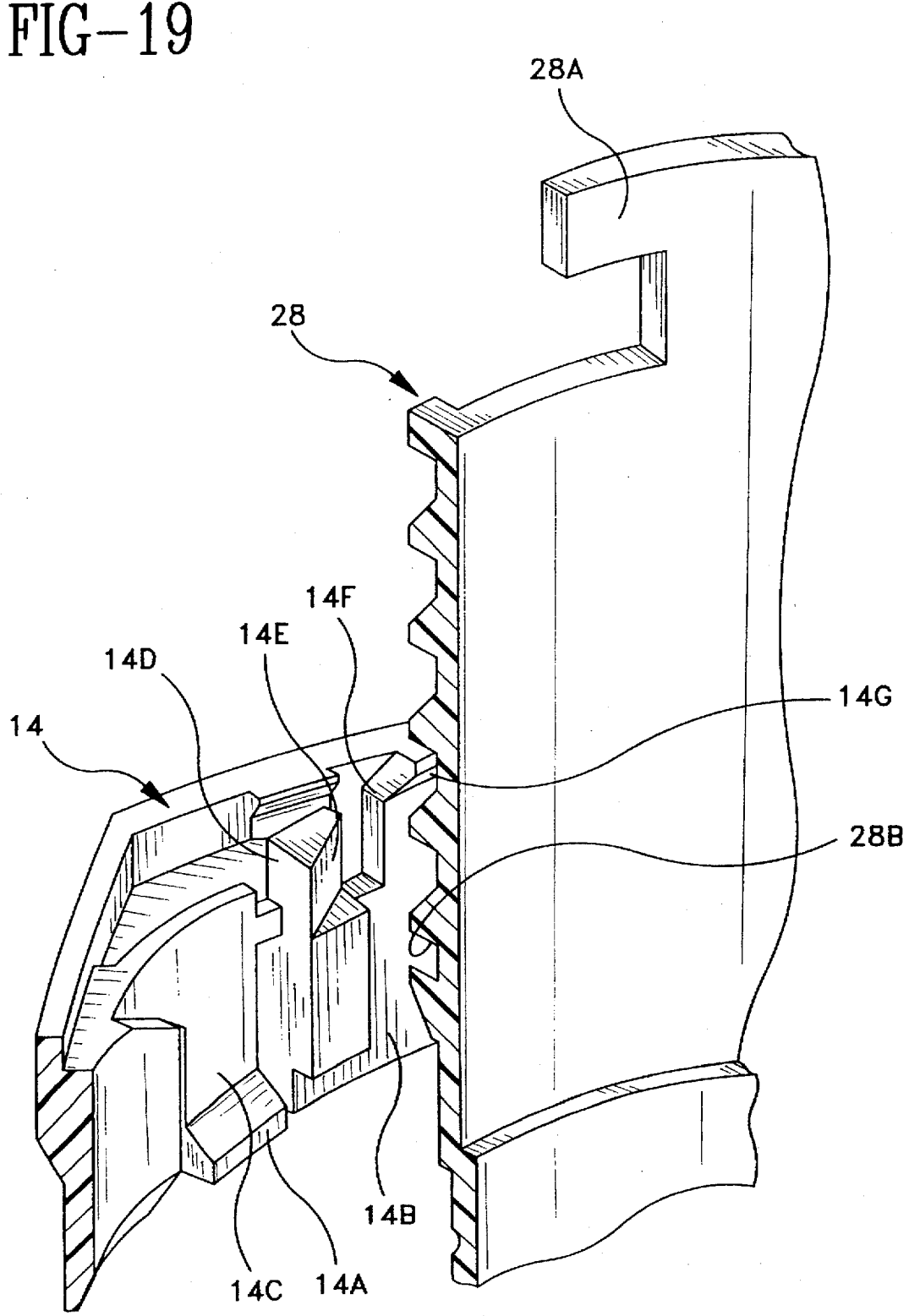
FIG. 19 is an enlarged, cutaway perspective showing an alternative embodiment of the sleeve adjoining a portion of the collar.

FIG. 19 illustrates an alternative embodiment of the invention where the sleeve rib 28C defines a plurality of incremental stops in the form of saw-toothed ratchet teeth 100. As the sleeve enters the collar, each of the stops engages the second pawl 14G, preventing sleeve withdrawal until the sleeve is rotated to the firing position. The walls defining the slot 14B and the sleeve rib are designed to permit sleeve rotation only upon full sleeve insertion. Rotation is then only possible in the direction of the inclined surface 14E and the first finger 14C.

The portion of the collar opposite the finger 14F is designed to interact with the deflectable finger 94 of the sleeve 28. It includes a notch bounded on one side by a shoulder 102 and on the opposite side by a ramp 104. When the sleeve is inserted into the collar and drive assembly housing, the finger 94, which is located one hundred eighty degrees from the rib 28C of the sleeve, enters the notch. Rotation of the sleeve into the firing position causes the ramp to bear against the relatively large projection 98 of the sleeve finger 94, thereby deflecting it radially inwardly. This causes the disengagement of the relatively small projection 96 and one of the radially inward projections 90 of the cap 16. The cap may accordingly be removed from the sleeve upon such disengagement by pulling it axially.

The injection device 10, when ready for use, includes a cartridge 30 containing the material to be injected. The piston 32 is located towards the rear end of the cartridge. The radially inwardly extending projection 24B of the plug 24 is located opposite the groove 54 in the rod 46. The driver 58 is coupled to the drive rod 46. The push-button 66 engages the driver 58, thereby preventing movement of the rod/driver assembly under the force of the constant force spring 56. The push-button cannot be depressed to release the rod/driver assembly as the sleeve projection 28A abuts the second engagement member 66B of the push-button.

The cap 16 is removed by pulling it forwardly along the longitudinal axis of the device. The shield 36 is removed with the cap. The device otherwise remains unchanged from its original position.

The end of the sleeve 28 is pressed against the epidermis, thereby causing a force to be exerted thereon. The sleeve moves rearwardly against the force of the sleeve spring 40 for several millimeters, at which time the rear portion 44 of the sleeve engages a stop 12C extending from the housing 12. This movement is sufficient to displace the sleeve projection 28A a sufficient distance that it no longer interferes with the downward movement of the push-button 66.

The projection 66C of the push-button is then pressed manually towards the housing, compressing spring 68 in the process. This causes displacement of the first engagement member 66A such that it no longer engages the driver 58. The driver 58 and rod 46 move as a unit under the constant force of the spring 56, causing the syringe assembly 20 (via the plug 24) to move forwardly, and the needle 38 thereof to penetrate the skin. The compression of spring 68 results in projection 66C being disposed against flats 74 of driver 58. The result is that, during the injection phase, projection 28A of the sleeve rests against engagement face 66D of second engagement member 66B so as to avoid premature withdrawal of sleeve 28 from the epidermis that might be caused, for instance, by any "kickback" forces exerted by constant force spring 56.

As the rod remains coupled to the driver, the piston 32 does not move. Once the needle has sufficiently penetrated the skin and underlying tissue, the projection 64 on the driver 58 engages the projection 70 extending inwardly from the housing 12. This causes the pivotable arm 62 of the driver to rotate, and the pawl 60 to move out of the notch 52. The driver 58 and rod are decoupled at this point, which is just prior to the bottoming of the sleeve spring 40.

The rod 46 is urged forwardly as the rear end of the constant force spring 56 rotates within the saddle 48. The rod now moves with respect to the driver 58, urging the piston 32 forwardly as fluid is displaced from the cartridge 30. The rod advances through the plug 24 as the groove 54 is aligned with the plug projection 24B. Movement of the rod continues until the piston 32 engages the end wall of the cartridge 30. The ramp 50 of the rod 46 engages the first engagement member 66A of the push-button near the end of its stroke, drawing the push-button entirely within the housing. This provides a visual end of dose indication. The sleeve 28 is released once the second engagement member 66B is sufficiently displaced with respect to the sleeve projection 28A.

Upon completion of the injection procedure, the device 10 is withdrawn from the body. The sleeve 28 moves forwardly under the force of the sleeve spring to again cover the needle 38, and is releasably locked in position by the pawl 14A on the first collar finger 14C. The push-button remains within the housing, and accordingly cannot be actuated until a new syringe assembly is installed.

The disposable portion of the device is disconnected from the reusable portion by grasping the sleeve 28 and pulling it in the axial direction. This causes the displacement of the pawl 14A from the notch 28B within the rib 28C of the sleeve. The cap 16 can be replaced before or after removal of the disposable portion of the device.

A new syringe assembly is installed by grasping the cap 16 and aligning the longitudinal rib 28C on the sleeve with the slot 14B in the collar. It can then be pushed into the housing until the cap 16 engages the collar 14. When aligned in this manner, the plug projection 24B is in opposing relation to the end surface 46A of the rod rather than the groove 54 within the rod. Insertion of the disposable portion of the device 10 accordingly causes the rod 46 to be pushed back into the housing 12. The wound end of the constant force spring 56 rotates in the saddle as the rod is pushed. The rim of the plug 24 pushes back the driver 58 during this procedure. The pawl 14G of the second finger 14F of the collar moves within the notch 28B in the rib 28C, preventing removal of the disposable portion of the device once fully inserted.

The disposable portion can be rotated about an arc of forty degrees once it is pushed as far back as possible. Because the driver is pushed back with the rod, the push-button 66 springs back into the actuatable position as it moves partially within the gap of the driver. The driver pawl 60 moves into one of the notches 52 in the rod. The particular notch to be engaged by the pawl is determined by the length of the plug 24. If the piston 32 is located closer to the needle end of the cartridge, the nose portion of the plug will be longer such that is adjoins, but does not contact, the piston. As discussed above, rotation of the sleeve with respect to the collar also causes the inward displacement of the sleeve finger 94 as the projection engages the ramp 104, thereby allowing the cap to be removed from the sleeve. The pawl 14G is simultaneously rotated out of engagement with the notch 28B in the sleeve rib, which allows the sleeve to be removed once the device has been fired.

It will be appreciated that various modifications can be made to the device for various purposes. The sleeve, for example, may include an engagement member and the housing a stop member, rather than vice versa, for preventing premature removal of the disposable portion of the device. While not preferred, a pair of springs could be used to drive the syringe assembly and piston, respectively. One or both springs could be constant force springs, preferably both. While it is also highly preferred that the drive assembly be rearmed upon insertion of the syringe assembly, this step could also be accomplished as a separate procedure. The use of a constant force spring facilitates the rearming procedure regardless of which approach is employed. Rearming may also be accomplished without directly engaging the drive rod. It is sufficient that the rod be driven back against the force of the drive spring, whether by direct engagement of the rod or via an intermediate structure.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An assembly for providing automatic injections, comprising:
    a drive assembly including a housing and a drive rod slidably mounted within said housing;
    a sleeve positionable within said housing;
    a syringe assembly slidably mounted within said sleeve, said syringe assembly including a cartridge and a piston slidably mounted within said cartridge, said drive rod being operatively associated with said syringe assembly when said sleeve is positioned within said housing;
    a spring for urging said drive rod towards said syringe assembly;
    one of said sleeve and said housing including a stop member and the other of said sleeve and said housing including an engagement member engageable with said stop member, said stop member and engagement member being arranged such that said engagement member engages said stop member when said sleeve is inserted along a longitudinal axis into said housing, thereby preventing withdrawal of said sleeve from said housing along said longitudinal axis, said engagement member being disengageable from said stop member upon rotation of said sleeve about said longitudinal axis to permit the sleeve to be removed from the housing.

2. An assembly as described in claim 1 wherein said engagement member comprises a pawl extending from said housing and stop member includes an abutment formed in an outer surface of said sleeve.

3. An assembly as described in claim 2 wherein said sleeve includes an elongate rib projecting radially outwardly therefrom, said stop member being formed on said elongate rib.

4. An assembly as described in claim 2 wherein said housing includes a second engagement member, said second engagement member being rotationally displaced from said pawl, said pawl being engageable with said stop member when said sleeve is in a first rotational position, said second engagement member being engageable with said stop member when said sleeve is in a second rotational position.

5. An assembly as described in claim 4 wherein said pawl is axially displaced with respect to said second engagement member.

6. An assembly as described in claim 1 wherein said housing includes a first end, a second end, and a collar mounted to said first end, said engagement member being integral with said collar.

7. An assembly as described in claim 6 wherein said collar includes an axial slot, said engagement member being aligned with said axial slot.

8. An assembly as described in claim 7 wherein said sleeve includes an elongate, radially outwardly extending rib, said rib defining said stop member, said rib being positionable within said axial slot.

9. An assembly as described in claim 1 wherein said housing includes an axial slot, said sleeve includes an elongate rib defining said stop member, and said engagement member is mounted to said housing in alignment with said axial slot.

10. An assembly as described in claim 1 including a push-button mounted to said housing and releaseably engageable with said drive rod and said sleeve.

11. An assembly as described in claim 1 wherein said housing includes an elongate body having a first end and a second end and a collar mounted to said first end of said body, said collar including a deflectable finger, said engagement member extending from said deflectable finger.

12. An assembly as described in claim 6 wherein said collar includes first and second deflectable fingers, a pawl extending from each of said fingers, said pawl extending from said second finger comprising said engagement member, said stop member being formed on an external surface of said sleeve, said stop member being engageable with said pawl extending from said second finger when said sleeve is in a first rotational position, said stop member being engageable with said pawl extending from said first finger when said sleeve is in a second rotational position.

13. An assembly as described in claim 12 wherein said first and second fingers are substantially parallel, said first finger having a free end adjoining a first end of said collar, said second finger having a free end adjoining a second end of said collar opposite from said first end.

14. An assembly as described in claim 1 wherein said sleeve includes an elongate rib defining a plurality of incremental stop members, said engagement member comprising a projection extending from an inner surface of said housing.

15. An assembly as described in claim 1 including a plug mounted to said cartridge, said drive rod being engageable with said plug when said sleeve is in a first rotational position, said drive rod being engageable with said piston when said sleeve is in a second rotational position, and wherein said stop member is engageable with said engagement member when said sleeve is in said first rotational position, said stop member being disengageable from said engagement member when said sleeve is rotated from said first rotational position to said second rotational position.

* * * * *